(12) United States Patent
Jadeed et al.

(10) Patent No.: US 7,914,901 B2
(45) Date of Patent: Mar. 29, 2011

(54) SUPPORT STRUCTURES FOR MOLDED PARTS

(75) Inventors: Nabeel Mark Jadeed, Cincinnati, OH (US); Charles Frank Benjey, Hamilton, OH (US); Donald F. Heaney, Philipsburg, PA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 976 days.

(21) Appl. No.: 11/612,670

(22) Filed: Dec. 19, 2006

(65) Prior Publication Data
US 2008/0142187 A1    Jun. 19, 2008

(51) Int. Cl.
*B22D 25/00* (2006.01)
*B22D 25/02* (2006.01)
*B22F 3/00* (2006.01)
*B22F 3/10* (2006.01)
*B22F 3/12* (2006.01)
*B22F 5/00* (2006.01)

(52) U.S. Cl. ........ 428/546; 428/548; 428/571; 428/572; 428/582; 428/591; 428/598

(58) Field of Classification Search ............... 428/546, 428/548, 571, 572, 582, 591, 598
See application file for complete search history.

(56) References Cited

U.S. PATENT DOCUMENTS

| 4,682,644 | A * | 7/1987 | Ueno ........................... 164/359 |
| 5,133,727 | A * | 7/1992 | Bales et al. ................... 606/170 |
| 5,308,576 | A * | 5/1994 | Green et al. .................... 419/38 |
| 6,725,901 | B1 | 4/2004 | Kramer et al. | |
| 2006/0047309 | A1 | 3/2006 | Cichocki | |
| 2006/0090603 | A1 | 5/2006 | Lewis et al. | |

FOREIGN PATENT DOCUMENTS
EP       0539809 A1    5/1993

OTHER PUBLICATIONS

European Search Report from corresponding European patent application No. EP07254916 dated Jun. 25, 2010, 5 pages.

* cited by examiner

*Primary Examiner* — Michael La Villa

(57) ABSTRACT

Structures and methods for hindering molded part deformation during densification are discussed. Such devices and techniques can help alleviate stresses that tend to result in part deformation during firing, sintering, or other densification processes, and thus reduce the need for secondary straightening operations post-densification. In some instances, a support structure is utilized to orient a molded greenbody in a preferred direction to reduce deformation during firing (e.g., orienting a thin tail section is a plane parallel to the direction of gravity). The support structure can also be part of, or the entirety of, a thermal mass to help alleviate stresses that lead to part deformation. Though such structures and methods can be used for any molded piece, it can be particularly used to create a portion, or an entirety of, a medical device such as a jaw of an surgical instrument.

8 Claims, 3 Drawing Sheets

SUPPORT STRUCTURES FOR MOLDED PARTS

FIELD OF THE INVENTION

The present invention relates to cast parts, and more specifically techniques for producing such parts to provide improved properties such as better alignment.

BACKGROUND OF THE INVENTION

During the firing of greenbodies to form sintered casted products, the greenbodies can undergo substantial shrinkage and deformation. For example, the casting of some medical components, such as a jaw of a device having forceps by metal injection molding (herein "MIM"), results in the intermediate formation of a molded greenbody that is subsequently fired to create the final product. During the heating and densification, the greenbody has a tendency to shrink. Such shrinkage can lead to an undesirable deformation of a greenbody. For example, when the greenbody has a section with a relatively more massive, larger cross section connected to a section with a relatively less massive, smaller cross section, the differential shrinkage between the sections can lead to differential stress formation between the sections that anisotropically distorts the shape of the fired product. In another example, sections of a greenbody that are extensions supported by a connection to a body can become misshapen during firing due to gravitational forces acting on the extension.

These potential misshapened products can result in the need for secondary straightening operations to correct variations in camber and/or tailwag effects after sintering. Beyond being time consuming, such operations also increase the cost of producing casted pieces. Furthermore, in some situations, secondary operations may not be able to adequately correct shape defects. In such cases, there is a decrease in product yield, which is directly related to loss of properly formed product.

Accordingly, a need exists for improved methods and devices that increase the quality of molded pieces, and in particular, decrease the probability of forming misshapened products during greenbody densification.

SUMMARY OF THE INVENTION

In one aspect, the invention pertains to cast products, and methods of casting products, that avoid distortion of the part during firing, sintering, or other densification processes.

Some exemplary embodiments are directed to cast products for forming a portion, or an entirety, of a medical device. Such cast products can include molded materials that have been sintered, fired, and/or densified, such as a sintered metal-injection molded material. The cast product can include a cast medical component, which can have a bulk portion connected to a tail portion (e.g., a flange structure). In some instances, the tail portion can have a smaller cross sectional area than the bulk portion. The cast product can also include a cast support structure. In some instances the support structure can be connected to a cast pouring cup portion. The cast support structure can be configured to orient the cast medical component to hinder misalignment of the component, e.g., between the bulk portion and tail portion during greenbody densification processing such as sintering. The support structure can be configured to hinder tailwag, camber misalignment, or both between the bulk and tail portions of a greenbody during densification. In another example, the cast support structure orients the tail portion in a vertical plane. The cast support structure can have a flat portion for contacting a surface to support the cast product, for example during densification.

In some embodiments, the cast products can be configured such that the cross sectional area of the tail portion to the cross sectional area of the bulk portion is a ratio in the range from about 0.1 to about 0.3. In other embodiments, the cast products can have a mass in the tail portion to a mass in the bulk portion in a ratio in the range from about 0.1 to about 0.3.

Other embodiments are directed to a molded greenbody. Such a greenbody can be a portion or an entirety of a medical device. The greenbody can include a molded portions with structures and/or functionality that includes any combination of the features described with respect to the cast products revealed herein. Molded portions, such as a product portion that can be embodied as a medical device piece upon densification, can be made of molding materials such as a metallic material with a binder.

Further embodiments are directed to methods of casting pieces such as a portion or an entirety of a medical device. A greenbody can be formed, which includes a molded support structure that can be connected to a product portion. The product portion can be molded, and can have a tail portion connected to a bulk portion. A molded pouring cup portion can also be include with the greenbody, with the molded support structure attached thereto. Greenbody formation can be performed using any number of techniques such as injection molding of a metal-containing composition. The formed greenbody can be positioned such that the molded support structure orients the molded product portion to hinder misalignment between the bulk portion and tail portion during sintering or some other densification process. For example, the greenbody can be positioned such that tailwag or camber misalignment or both effects are hindered during densification. Greenbody positioning can include supporting the molded product portion such that the tail portion does not directly contact a surface supporting the greenbody. In one embodiment, positioning the greenbody includes resting the molded support structure on a surface to support the greenbody during densification. The greenbody can then be densified using sintering, firing, or some other densification process. A degating step can also be included to separate a product portion of the densified greenbody from the remaining portions of the densified material.

BRIEF DESCRIPTION OF THE DRAWINGS

The invention will be more fully understood from the following detailed description taken in conjunction with the accompanying drawings (not necessarily to scale), in which.

DETAILED DESCRIPTION OF EMBODIMENTS OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Some embodiments are directed to molded greenbodies, which can be configured to hinder misalignment of the greenbody during sintering or some other densification process. In general, a greenbody is a molded body whose formation is typically an intermediate step of a process for forming a final molded part. The greenbody is typically densified through any number of processes such as a thermal process, which results in the final molded part having desired final properties (e.g., higher strength and density relative to the greenbody). Though molded greenbodies can be formed in any particular shape or size, some embodiments are specifically directed to such greenbodies that form a part, or the entirety of, a medical device (e.g., a forcep or jaw of a medical apparatus such as a stapler or grasping unit).

Figure 1:
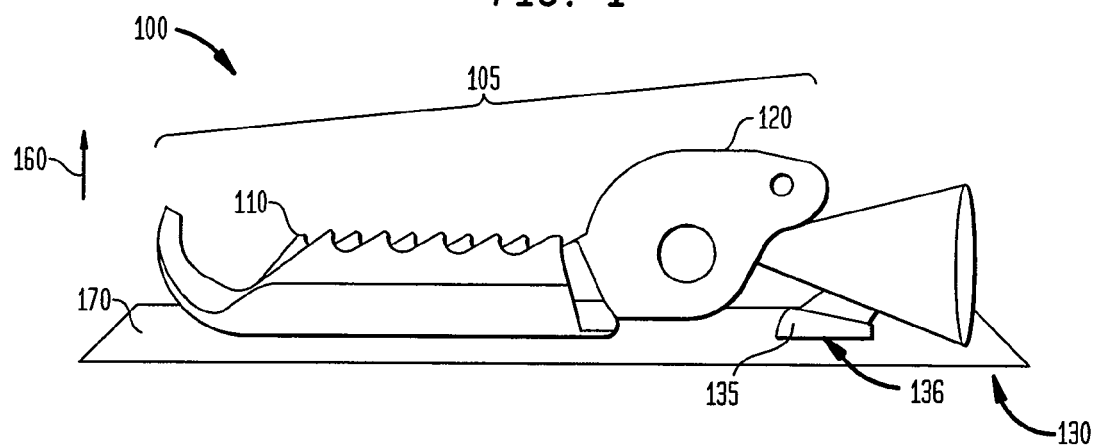
FIG. 1 is a schematic perspective view of a greenbody including a portion of a jaw of a medical device, consistent with embodiments of the invention.

An exemplary embodiment of a formed greenbody is depicted in FIG. 1. The molded greenbody 100 shown in FIG. 1 includes a jaw product portion 105 having a bulk portion 110, which can be attached to a tail portion 120 embodied as a flange. The greenbody 100 also includes a pouring cup portion 130 that is connected to the jaw 105. As depicted in FIG. 1, the pouring cup portion 130 includes a molded support structure 135, which is particularly shown here to be a footed structure with a flat portion 136. The pouring cup portion 130 can be the result of the portion of a molded body that conforms to the inlet of a mold into which molding material is inserted. After greenbody firing, the pouring cup portion 130, along with the casted support structure 135, is typically removed. Though the embodiment of FIG. 1 utilizes the support structure and pouring cup portion as one unit, other embodiments can have a support structure connected to the product portion without a pouring cup structure.

In general, a support structure can be configured to orient the greenbody to hinder misalignment between a bulk portion and a tail portion. For example, with respect to the jaw 105 shown in FIG. 1, the molded support structure 135 is adapted to hold the jaw 105 in a position such that the plane of the tail portion 120 is oriented to extend in a plane that is parallel to the vertical direction 160. That is, the tail portion 120 extends in a plane that is perpendicular to a horizontally oriented resting surface 170 on which the support structure 135 rests. This arrangement can help stabilize the tail portion 120 such that it is unable to move or change orientation during densification. Without the presence of the support structure 135, the tail portion 120 could deform or otherwise be reoriented such that the tail portion 120 could drift during densification relative to the bulk portion 110. For example, if the jaw 100 is rolled relative to the orientation shown in FIG. 1 such that the tail portion 120 is parallel to the support surface 170, densification could result in the tail portion 120 being displaced toward the surface 170 by gravity, and being misaligned relative to the bulk portion 110 upon being hardened.

A support structure, or the combination of a molded pouring cup and support structure as shown in FIG. 1, can also act as a thermal mass to help distribute mass more evenly over the entire greenbody. With respect to FIG. 1, without the molded pouring cup portion 130, the difference in the relative mass between a tail portion 120 and a bulk portion 110 can be substantial. Such a mass distribution can promote deformation of the product part 105 because of anisotropic shrinkage (i.e., differential shrinkage volumes in the portions due to differences in mass). By utilizing another mass, in the form of a pouring cup structure 130 that is attached to the tail portion 120, the total mass of the greenbody can be more evenly distributed. Accordingly, in some embodiments, a greenbody can include a product portion having a more massive product section and a less massive product section, where the less massive product section is coupled to a section having a support structure acting to distribute mass over the greenbody. In such embodiments, the ratio of the mass of the more massive portion of the product to the less massive portion of the product can be in a range from about 0.1 to about 0.3.

In some embodiments, a support structure can act to hinder part deformation during greenbody densification where the greenbody has at least two portions: one with a relatively larger cross section relative to another portion with a relatively smaller cross section. The cross section can be defined by providing some representative cross sectional area for each of the two portions. Such definitions can utilize any particular cross section of the portion, or can average the cross section using techniques known to those skilled in the art. By attaching the support structure to the portion with a smaller cross section, the potential of stress mismatch leading to part deformation can be reduced. Accordingly, some embodiments are directed to a greenbody where the ratio of the cross sectional area of the smaller section to the cross sectional area of the larger section is in the range from about 0.1 to about 0.3.

Figure 2:
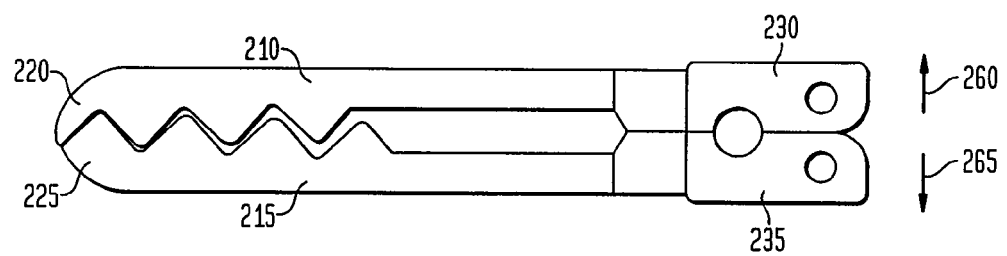
FIG. 2 is a schematic side view of a set of jaws of a portion of a medical device, in which the jaws have substantially perfect camber.
Figure 3:
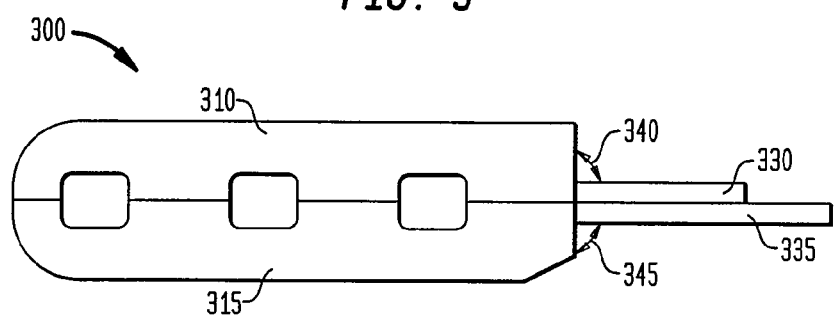
FIG. 3 is a schematic side view of a set of jaws of a portion of a medical device, in which the jaws do not exhibit substantial tailwag.

Using molded greenbodies consistent with embodiments described herein can reduce/eliminate the need for secondary straightening, or other shape-changing, operations. Thus, finished cast pieces such as medical device parts can be created that can have reduced, or substantially no, tailwag or camber misalignment between a bulk portion and a tail portion of the casted piece. FIG. 2 depicts an exemplary set of jaws of a device with substantially perfect camber, i.e., the distal tips 220 of the jaws 210, 215 contact one another when the jaws 210, 215 are in the closed position. If the camber of the jaws 210, 215 were distorted, e.g., each jaw being arced away from the toothed surface, the jaws 210, 215 would not meet at their respective distal tips 220, 225 as desired. Thus, a secondary procedure of aligning the tail ends 230, 235 would be required. FIG. 3 depicts an exemplary device 300 having substantially perfect tailwag. The tail ends 330, 335 of jaws 310, 315 are oriented relative to jaws 310, 315 such that the respective angles 340, 345 are each substantially 90 degrees. This allows the jaws 310, 315 to fully contact along the a contact surface extending through a plane where the jaws 310, 315 meet. If the respective angles 340, 345 were not 90 degrees, owing to e.g., distortion in the tail sections 330, 335, then a secondary operation would be required to provide the 90 degree angle. The devices and methods discussed herein can help alleviate such a situation.

Some embodiments are directed to densified casted products, such as products that form a portion or an entirety of a medical device. Such casted products can be the result of densifying molded greenbodies, such as those that are subjected to firing, sintering, or some other densification process.

The cast products can include any combination of the structural and/or functional features discussed with respect to various types of molded greenbodies disclosed herein. For example, the casted product can include a cast medical component having bulk and tail portions; and a cast pouring cup portion connected to the cast medical component, the pouring cup portion including a cast support structure configured to hinder misalignment of the medical component during greenbody densification.

Figure 4:
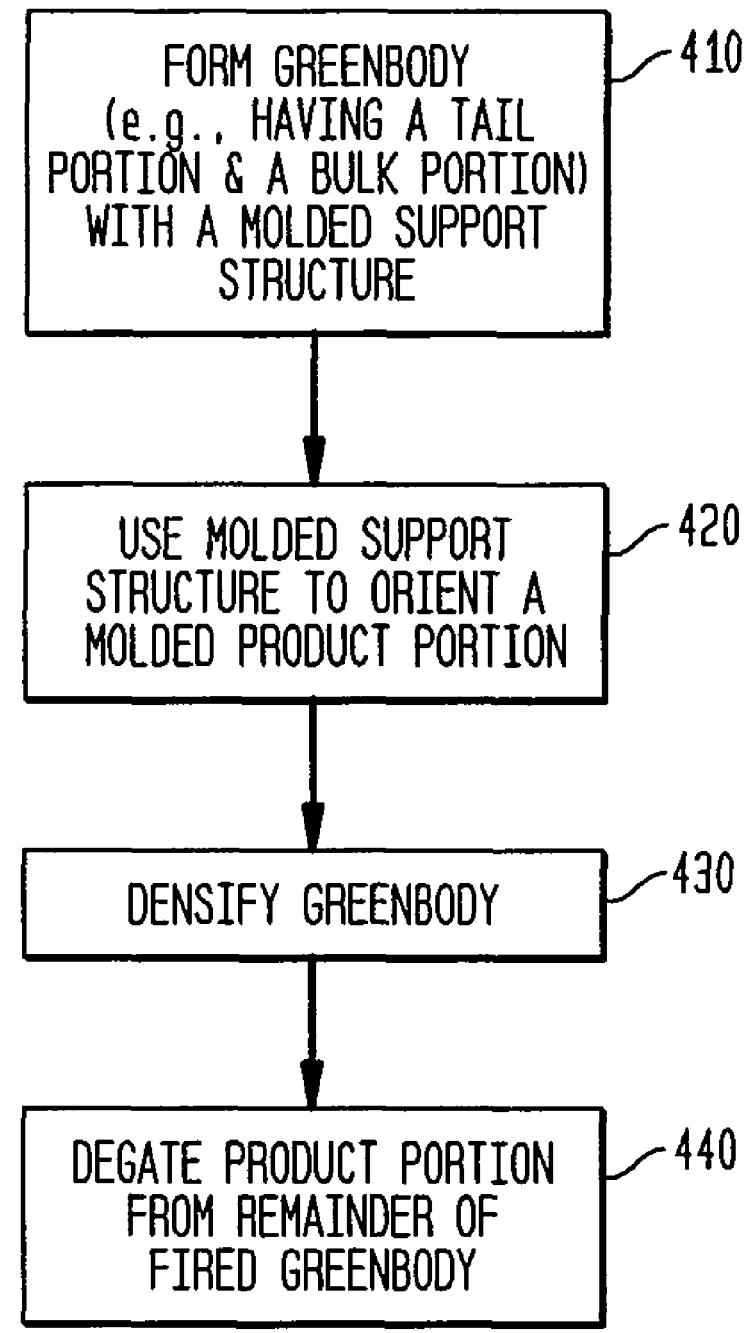
FIG. 4 is a flow diagram of a method for casting a product, consistent with embodiments of the invention.

Other embodiments are directed to methods of casting a device or a portion of a device, such as a medical device. A flow diagram of an exemplary casting process is shown in FIG. 4. The method 400 includes a step of forming a greenbody that includes a molded support structure 410. In some embodiments, the greenbody can include a molded product portion and a molded support structure; the latter can be incorporated as a portion of a molded pouring cup portion in which the combination together can act as a thermal mass during densification. In some embodiments, the molded product portion can include a bulk portion and a tail portion. The tail portion can be configured to have a smaller thermal mass and/or a smaller cross sectional area relative to the bulk portion. As well, the tail portion can be configured to be connected to the molded pouring cup portion and/or to the molded support structure.

A molded greenbody can be formed using a variety of methods, and/or a variety of materials. For example, the greenbody can be formed by injection molding of a metal powder, polymer, and binder mixture into a mold. Those skilled in the art will appreciate that the embodiments of the present application are not necessarily limited by the methods utilized to form the greenbody, or the materials of the greenbody, and that the current application contemplates the use of all such techniques and materials. The types of formation processes that be used can include any of the techniques discussed herein (e.g., MIM) and those understood by persons skilled in the art.

Upon forming a greenbody, the molded support structure can be used to orient the molded product portion 420. For example, a greenbody can be positioned to hinder misalignment of a molded product portion during densification (e.g., sintering). For instance, when the molded product portion includes a bulk portion and a tail portion, the greenbody can be oriented to hinder misalignment between the bulk and tail portions. The orientation can be such that either tailwag, camber, or both, are controlled in desirable manners. This can be achieved by a variety of techniques such as positioning the molded product portion such that the tail portion does not contact a supporting surface of the greenbody during densification and/or resting the greenbody on a surface such that the support structure contacts a surface during greenbody densification.

After orienting the greenbody, the body is densified 430 using any of the techniques discussed herein, or other techniques for densifying greenbodies known to those skilled in the art such as sintering, firing, etc. Such densification can take place to form a final casted piece. In some embodiments, the use of the steps of the method 400 can alleviate the need for performing secondary straightening operations after densification 430. Optionally, the product portion of a fired product can be degated from the remainder (e.g., cutting off a cup portion) of the fired portion 440 to yield the product piece.

EXPERIMENTS

The following experimental results are provided to illustrate some aspects of the present application. The experiments, however, are not intended to limit the scope of any embodiment of the invention.

An experiment was conducted to assess the effectiveness of a tail support in reducing either tailwag or camber during sintering of a molded jaw piece. Twenty jaw pieces resembling the jaw piece depicted in FIG. 1 were molded and sintered. Ten of the jaw pieces included a tail support 136, as depicted in FIG. 1, and ten jaw pieces were created without a support 136.

Figure 5:
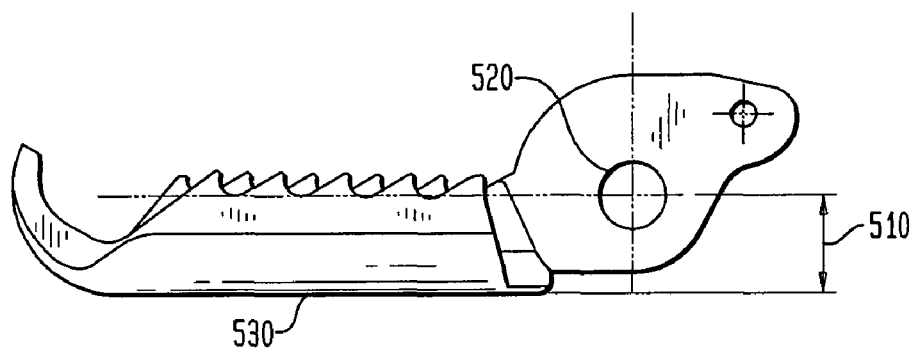
FIG. 5 presents a side view of a portion of the jaw depicted in FIG. 1 showing a camber measure used in some experiments described herein.
Figure 6:
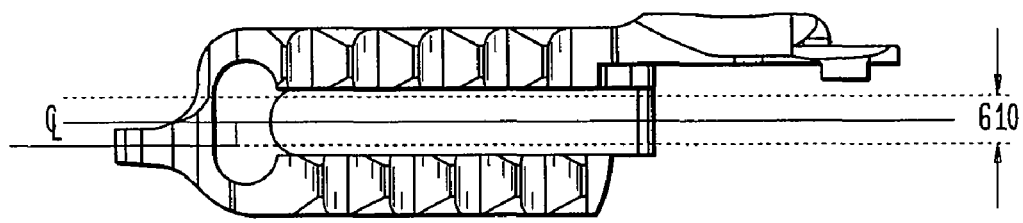
FIG. 6 presents a top view of a portion of the jaw depicted in FIG. 1 showing a tailwag measure used in some experiments described herein.

For each completed jaw piece, measurements of tailwag and camber were taken. The measure of camber, as depicted by the side view of a jaw shown in FIG. 5, was taken as the vertical distance 510 between the centerline of the large diameter hole 520 and the bottom edge of the jaw back 530. With perfect camber, the vertical distance 510 was designed to be 0.049 inches. The measure of tailwag, as depicted by the top view of the jaw shown in FIG. 6, is defined by the parallelism dimension 610, which is defined to be 0.001 inches with no tailwag present.

TABLE 1

Raw Data of Tailwag and Camber Measurements

| Support | Tailwag (in) | Camber (in) |
|---|---|---|
| Yes | 0.0016 | 0.0465 |
| Yes | 0.0009 | 0.0465 |
| Yes | 0.0009 | 0.0468 |
| Yes | 0.0013 | 0.0461 |
| Yes | 0.0008 | 0.0464 |
| Yes | 0.0017 | 0.0469 |
| Yes | 0.0012 | 0.0466 |
| Yes | 0.0014 | 0.0466 |
| Yes | 0.0011 | 0.047 |
| Yes | 0.0016 | 0.0465 |
| No | 0.0015 | 0.0463 |
| No | 0.0015 | 0.0473 |
| No | 0.0019 | 0.0469 |
| No | 0.0015 | 0.0463 |
| No | 0.0018 | 0.0461 |
| No | 0.0008 | 0.0464 |
| No | 0.0015 | 0.0472 |
| No | 0.0016 | 0.0471 |
| No | 0.0014 | 0.0463 |
| No | 0.0014 | 0.0475 |

The data for the experiments is shown in Table 1. Analyses were performed on the tailwag and camber data to determine if overall differences exist between jaw pieces that included a support and jaw pieces lacking a support.

With respect to tailwag, jaw pieces created with a support exhibited an average tailwag dimension of 0.046590 inches as compared to an average value of 0.046740 inches for pieces created without the support, i.e., the support pieces showed less tailwag.

With respect to camber, the average value of the camber measure was slightly smaller for pieces with a support vis-à-vis pieces without a support. However, the variance in the camber measures were appreciably different. In particular, a statistical Lavene's test performed on the camber data showed a p-value of 0.004. Accordingly, sufficient evidence existed to conclude that pieces having a support showed statistically less variance in camber measure than pieces having no support with 95% confidence. Thus, pieces created with a support were subject to less variation in camber than pieces created without a support.

One skilled in the art will appreciate further features and advantages of the invention based on the above-described embodiments. Accordingly, the invention is not to be limited by what has been particularly shown and described, except as indicated by the appended claims. Indeed, as previously mentioned, one or more of the techniques can be practiced alone, or combined with any others to provide product cast pieces (e.g., combining angling of side runners with positioning the closed-end side runner at least two cross sectional lengths from the closed end of a sprue). All publications and references cited herein are expressly incorporated herein by reference in their entirety.

What is claimed is:

1. A cast product for forming at least a portion of a medical device, comprising:
   a cast medical component comprising a bulk portion and a tail portion connected together, the tail portion having a smaller cross sectional area than the bulk portion;
   a cast pouring cup portion connected to the cast medical component, the cast pouring cup including a cast support structure configured to orient the cast medical component to hinder misalignment between the bulk portion and tail portion during greenbody densification;
   wherein the cast product comprises a densified greenbody.

2. The cast product of claim 1, wherein the cast support structure is configured to hinder at least one of tailwag and camber misalignment between the bulk portion and the tail portion during greenbody sintering.

3. The cast product of claim 2, wherein the cast support structure orients the tail portion in a vertical plane.

4. The cast product of claim 1, wherein the cross sectional area of the tail portion to the cross sectional area of the bulk portion is a ratio in the range from about 0.1 to about 0.3.

5. The cast product of claim 1, wherein a mass of the tail portion to a mass of the bulk portion is a ratio in the range from about 0.1 to about 0.3.

6. The cast product of claim 1, wherein the cast product comprises a sintered metal-injection molding material.

7. The cast product of claim 1, wherein the tail portion comprises a flange structure.

8. The cast product of claim 1, wherein the cast support structure comprises a flat portion for contacting a surface to support the cast product.

\* \* \* \* \*